(12) United States Patent
Gibson et al.

(10) Patent No.: US 7,695,740 B2
(45) Date of Patent: Apr. 13, 2010

(54) SYNTHETIC CALCIUM PHOSPHATE COMPRISING SILICON AND TRIVALENT CATION

(76) Inventors: Iain Ronald Gibson, 48 Glenury Crescent, Aberdeen AB39 3LF (GB); Janet Mabel Scott Skakle, 48 Glenury Crescent, Aberdeen AB39 3LF (GB); Jennifer Anne Stephen, 28 Seaview Drive, Bridge of Don, Aberdeen AB23 8RG (GB); Thomas Buckland, 99 Kilmorie Road, Forest Hill, London SE23 2SP (GB)

( * ) Notice: Subject to any disclaimer, the term of this patent is extended or adjusted under 35 U.S.C. 154(b) by 215 days.

(21) Appl. No.: 11/168,420

(22) Filed: Jun. 29, 2005

(65) Prior Publication Data
US 2007/0003634 A1    Jan. 4, 2007

(51) Int. Cl.
*A61F 2/00*     (2006.01)
*A61K 33/42*    (2006.01)
*A61K 31/28*    (2006.01)
*A01N 59/26*    (2006.01)
*A01N 55/00*    (2006.01)

(52) U.S. Cl. .................. 424/602; 424/423; 514/492

(58) Field of Classification Search ....................... None
See application file for complete search history.

(56) References Cited

U.S. PATENT DOCUMENTS 6,312,468 B1 * 11/2001 Best et al. ................ 623/16.11

OTHER PUBLICATIONS

Abstract: Ito American Mineralogist 1968, 53(516), 890-907) 1 page.*
Webster et al. Journal of Biomedical Materials Research 2002, 59(2), 312-217.*
J. Ito, et al. "Silicate Apatites And Oxyapatites", American Mineralogist, Washington, DC, May 1968, vol. 53, No. 516, pp. 890-907.
J. Imbach, et al., "Synthesis And NMR Characterization (1H And 31P MAS) of the Flourine-Free Hydroxylapatite-Britholite-(Y) Series", American Mineralogist, Washington, DC, 2002, vol. 87, No. 7, pp. 947-957.
D. Arcos, et al., "Crystal-chemical characteristics of silicon-neodymium substituted hydroxyapatites studied by combined X-ray and neutron powder diffraction", Chemistry of Material American Chem. Soc., Jan. 11, 2005, vol. 17, pp. No. 1, pp. 57-64.
L.V. Zaslavskaya, et al., "Synthesis of the modified bioactive calcium hydroxyapatite", Science for Materials in the Frontier of Centuries: Adavantages and Challenges, International Conference, KYIV, Ukraine, 2002, pp. 281-282.
R. El Ouenzerfi, et al., "Investigation of the CaO-La203-SiO2-P205 quaternary diagram. Synthesis, existence domain, and characterization of apatitic phosphosilicates", Solid State Ionics, North Holland Pub. Company, Jan. 2003, vol. 156, pp. 209-222.
R. El Ouenzerfi, et al., "Luminescent properties of rare-earth (Eu<3+>, Eu<2+> and Ce<3+>) doped apatitc oxyphosphosilicates", Journal of Luminescence, May 2003, vol. 102-103, pp. 426-433.
D. Arcos, et al., "Silicon incorporation in hydroxylapatite obtained by controlled crystallization", Chem. Mater.; Chemistry of Materials, Jun. 1, 2004, vol. 16, No. 11, pp. 2300-2308.
Maria Vallet-Regi et al., "Silicon substituted hydroxyapatites. A method to upgrade calcium phosphate based implants", J. Mater. Chem.; Journal of Materials Chemistry, Apr. 21, 2005, vol. 15, No. 15, pp. 1509-1516.

* cited by examiner

*Primary Examiner*—Ernst V Arnold
(74) *Attorney, Agent, or Firm*—Bacon & Thomas, PLLC (57) ABSTRACT

Biomedical materials and, in particular, to substituted calcium phosphate (e.g. apatite and hydroxyapatite) materials for use as synthetic bone. A synthetic calcium phosphate comprising silicon and a trivalent cation having a formula $Ca_{10-y}M_y(PO_4)_{6-x}(SiO_4)_x(OH)_{2-x+y}$ where M is a trivalent cation, $0<x<1.3$ and $0<y<1.3$. The trivalent cation is one or more of yttrium, scandium, aluminium and the Lanthanide elements. Preferably, the trivalent cation is or comprises yttrium. The trivalent cation is believed to substitute for the calcium ion in the hydroxyapatite lattice.

52 Claims, 6 Drawing Sheets

SYNTHETIC CALCIUM PHOSPHATE COMPRISING SILICON AND TRIVALENT CATION

The present invention relates to biomedical materials and, in particular, to substituted calcium phosphate (eg apatite and hydroxyapatite) materials for use as synthetic bone.

The combined affects of an ageing population and greater expectations in the quality of life have resulted in an increasing global demand for orthopaedic implants for the replacement or augmentation of damaged bones and joints. In bone grafting current gold standards include the use of autograft and allograft but these methods are increasingly recognised as non-ideal due to limitations in supply and consistency. Ceramics have been considered for use as bone graft substitutes to replace or extend traditional bone grafts for over 30 years. In particular, calcium phosphates such as hydroxyapatite have been promoted as a result of their osteoconductive properties.

Accordingly, as surgical technique and medical knowledge continue to advance, there has been a growth in the demand for synthetic bone replacement materials. Consequently, there is an increasing interest in the development of synthetic bone replacement materials for the filling of both load bearing and non-load bearing osseous defects, such as in joint and facial reconstruction.

The biocompatibility of hydroxyapatite, coupled with the similarities between the crystal structure of hydroxyapatite and the mineral content of bone, has led to great interest in hydroxyapatite as a material for the augmentation of osseous defects. The apatite group of minerals is based on calcium phosphate, with stoichiometric hydroxyapatite having a molar ratio of Ca/P of 1.67. Hydroxyapatite has the chemical formula $Ca_{10}(PO_4)_6(OH)_2$.

Silicate-substituted hydroxyapatite compositions provide attractive alternatives to stoichiometric hydroxyapatite as a bone replacement material. Silicon has been shown to enhance the rate and quality of bone healing when combined with calcium phosphate bone grafts, resulting in faster bone bonding between implant and host. PCT/GB97/02325 describes a silicate-substituted hydroxyapatite material.

A problem exists, however, because the substitution of silicate into the hydroxyapatite does have a compositional limit. When the level of silicate substitution passes this limit, the hydroxyapatite may become thermally unstable at typical sintering temperatures (for example approximately 1200° C. or above). This can result in the formation of secondary phases such as, for example, tricalcium phosphate (TCP), which for certain applications may be undesirable. The substitution limit for silicate substitution into the hydroxyapatite lattice is approximately 5.3 wt % (corresponding to 1.6 wt % silicon).

The present invention aims to address at least some of the problems associated with the prior art and/or to provide novel biomedical materials based on various calcium phosphate materials.

Accordingly, the present invention provides a synthetic calcium phosphate-based biomedical material comprising silicon and a trivalent cation.

The biomedical material according to the present invention is based on a calcium phosphate material such as, for example, hydroxyapatite or apatite.

The biomedical material according to the present invention preferably comprises a compound having the general chemical formula:

where M is a trivalent cation, 0<x<1.3 and 0<y<1.3. Preferably, 0<x<1.1, more preferably, 0.5<x<1.1. Preferably, 0<y<1.1, more preferably 0.5<y<1.1. It is also preferable that $x \geqq y$.

The trivalent cation is preferably selected from one or more of yttrium, scandium, aluminium and the Lanthanide elements. Preferably, the trivalent cation is or comprises yttrium.

The trivalent cation is believed to substitute for the calcium ion in the hydroxyapatite lattice. The silicate ion is believed to substitute for the phosphate ion in the hydroxyapatite lattice.

For the avoidance of doubt, the term silicate-substituted as used herein also encompasses silicon-substituted. Likewise, silicon-substituted as used herein also encompasses silicate-substituted.

In one embodiment of the present invention, where an essentially phase pure material is required, the phase purity of the material is preferably at least 95%, more preferably at least 97%, still more preferably at least 99%. In this case the material is substantially free of any secondary phases. It will be appreciated that unavoidable impurities may, however, be present. As will be appreciated, the phase purity of the biomedical material can be measured by conventional X-ray diffraction techniques.

In another embodiment, where the presence of secondary phases does not present a problem, the material may further comprise one or more secondary phases such as, for example, tricalcium phosphate (eg α-TCP and/or β-TCP). Accordingly, the present invention also provides for biphasic and multiphase materials. The secondary phases may be present in an amount of up to 60 wt. %, more typically up to 40 wt. %, still more typically up to 20 wt. %.

The biomedical material according to the present invention may be used as a synthetic bone material, a bone implant, a bone graft, a bone substitute, a bone scaffold, a filler, a coating or a cement. The biomedical material may be provided in a porous or non-porous form. The biomedical material may be provided in the form of a composite material, for example in conjunction with a biocompatible polymer.

The present invention also provides a biomedical material comprising a synthetic trivalent cation-silicate co-substituted calcium phosphate-based material. Examples include trivalent cation-silicate co-substituted hydroxyapatite and apatite materials. The trivalent cation is preferably selected from one or more of yttrium, scandium, aluminium and the Lanthanide elements. More preferably, the trivalent cation is or comprises yttrium. The preferred features described above are also applicable either singularly or in combination to this aspect of the present invention.

The biomedical material according to the present invention may be prepared by an aqueous precipitation method or a solid-state method such as, for example, a hydrothermal method. The aqueous precipitation technique is, however, preferred. Accordingly, the present invention also provides a process for the synthesis of a calcium phosphate-based biomedical material comprising silicon and a trivalent cation, the process comprising:

providing calcium or a calcium-containing compound, a trivalent cation-containing compound, a phosphorus-containing compound and a silicon-containing compound; and forming a precipitate by reacting the compounds in an aqueous phase at an alkali pH.

The process may be used to synthesise hydroxyapatite and apaptite materials comprising silicon and a trivalent cation.

The process according to the present invention is preferably an aqueous precipitation process.

Preferably, the calcium-containing compound comprises a calcium salt. The calcium salt may, for example, be selected from one or more of calcium hydroxide, calcium chloride, calcium nitrate and/or calcium nitrate hydrate.

Preferably, the trivalent cation-containing compound comprises a compound of yttrium. The yttrium-containing compound may, for example, be selected from one or both of yttrium chloride and/or yttrium nitrate, preferably $Y(NO_3)_3 \cdot XH_2O$.

The yttrium is preferably present in the biomedical material (i.e. the final product) in an amount of up to 13 weight percent, more preferably up to 12 weight percent. This is typical if the material is an essentially phase pure material as discussed above. On the other hand, if the material comprises one or more secondary phases, then the amount of yttrium in the material may exceed 13 weight percent and may be present in an amount of up to 20 weight percent.

Preferably, the silicon-containing compound comprises a silicate. More preferably, the silicate is selected from one or both of tetraethyl orthosilicate (TEOS) and/or silicon acetate.

The silicate is preferably present in the material (i.e. the final product) in an amount of up to 13 weight percent (which correlates to 4 weight percent as silicon), more preferably up to 12 weight percent (which correlates to 3.66 weight percent silicon). Again, this is typical if the material is an essentially phase pure material as discussed above. On the other hand, if the material comprises one or more secondary phases, then the amount of silicate in the material may exceed 13 weight percent and may be present in an amount of up to 20 weight percent.

Preferably, the phosphorus-containing compound is selected from one or both of a phosphate salt and/or a phosphoric acid. More preferably, the phosphorus-containing compound is selected from one or both of ammonium phosphate and/or phosphoric acid.

In one embodiment, the silicon-containing compound and the trivalent cation-containing compound are preferably supplied in substantially equimolar quantities with respect to the amount of silicon and the quantity of the trivalent cation. In an alternative embodiment, the silicon-containing compound is supplied in a greater molar quantity than the trivalent cation compound, with respect to the quantity of silicon and the quantity of the trivalent cation.

The process according to the second embodiment of the present invention is preferably carried out at an alkaline pH. Preferably, the pH is from 8 to 13. More preferably, the pH is from 10 to 12.

In order to adjust the pH of the solution to the desired pH, an alkali is preferably added to the solution. The alkali may be, for example, ammonium hydroxide or concentrated ammonia.

The process according to the present invention preferably comprises first forming under ambient conditions (although this step can be performed at a temperature up to about 100° C.) an aqueous suspension comprising calcium or the calcium-containing compound (e.g. $Ca(OH)_2$) and the trivalent cation-containing compound (e.g. $Y(NO_3)_3 \cdot XH_2O$). Next, an aqueous solution of the phosphorus-containing compound (e.g. $H_3PO_4$) is slowly added to the suspension with stirring. Finally, an aqueous solution of the silicon-containing compound (e.g. $Si(OC_2H_5)_4$=TEOS) is added slowly with stirring (instead, the aqueous solution of the phosphorus-containing compound can be mixed with the aqueous solution of the silicon-containing compound, and the combination then added slowly with stirring the suspension). The pH is monitored and maintained at an alkali pH, preferably from 11 to 13, using, for example, concentrated ammonia solution. The total mixture is then left to age and precipitate, which typically takes up to 12 to 24 hours.

Once the precipitate has been formed and aged it may be dried, heated and/or sintered. Preferably, it is first dried by heating it to a temperature of up to 100° C. This may then be followed by heating a temperature in the range of from 800° C. to 1500° C., more preferably from 1000° C. to 1350° C., and even more preferably from 1200° C. to 1300° C., in order to sinter the material. The dried precipitate is preferably ground into a powder prior to the sintering step.

The aforementioned process may be used to prepare an essentially phase pure material as herein described.

If it is desired to produce a biphasic or multiphase material, for example an yttria/silicate co-substituted biphasic composition, rather than a single phase yttria/silicate co-substituted hydroxyapatite, a number of steps may be used independently or in combination. The following are examples. First, the pH of the precipitation may be lowered to from 11-13 to 8-10. This has been found to promote the precipitation of a yttria/silicate co-substituted cation-deficient apatite composition, which forms a biphasic yttria/silicate co-substituted composition on heating. Secondly, the reaction mixture may be adjusted so that the relative amount of cations added, either calcium salt or yttrium salt or a combination of the two, is lowered, to promote the precipitation of a yttria/silicate co-substituted cation-deficient apatite composition. Again, this will form a biphasic yttria/silicate co-substituted composition on heating. Thirdly, the reaction mixture may be adjusted so that the relative amount of anions added, either phosphate salt or silicate salt or a combination of the two, is lowered, to promote the precipitation of a yttria/silicate co-substituted cation-deficient apatite composition, which will form a biphasic yttria/silicate co-substituted composition on heating. Fourthly, the pH may be lowered in combination with the alteration of the reaction mixture composition, to produce a yttria/silicate co-substituted cation-deficient apatite composition, which will form a biphasic yttria/silicate co-substituted composition on heating. It will be appreciated that yttria has been quoted by way of example.

In addition to these methods, increasing the amount of silicate/yttria substitution beyond the limits quoted to produce a single phase hydroxyapatite-like composition will also result in a biphasic yttria/silicate co-substituted composition on heating. Additionally, heating any composition to sufficiently high temperatures ($\geqq 1400°$ C.), or for prolonged heating times at high temperatures will also generally result in a biphasic yttria/silicate co-substituted composition on heating. Again, it will be appreciated that yttria has been quoted by way of example.

The present invention also provided a method of stabilizing a silicon-substituted hydroxyapatite material, which method comprises co-substituting a trivalent cation into the lattice. Preferably, the trivalent cation is selected from one or more of yttrium, scandium, aluminium and the Lanthanide elements. Preferably, the trivalent cation is yttrium.

The present invention will now be described further with reference to the following preferred embodiments.

To enable greater levels of silicate substitution into the calcium phosphate lattice (eg hydroxyapatite or apatite), the present invention provides a co-substitution method, whereby yttrium (or other trivalent cations suitable for substitution for the calcium ions) is co-substituted with the silicate ions. Two distinct mechanisms are possible. The first essentially negates the loss of hydroxyl (OH) groups from the hydroxyapatite lattice to balance charge, as the equimolar substitution of yttrium and silicate ions for calcium and phosphate ions balances charge:

$$Y^{3+} + SiO_4^{4-} \rightarrow Ca^{2+} + PO_4^{3-} \qquad (1)$$

This may be summarised by the general equation:

$$Ca_{10-x}Y_x(PO_4)_{6-x}(SiO_4)_x(OH)_2$$

The second substitution, where proportionally less yttrium ions are co-substituted with silicate ions, which results in the reduction in the level of OH groups to balance the charge (for an example where the molar amount of yttrium is half the molar amount of silicate being substituted):

$$0.5Y^{3+} + SiO_4^{4-} \rightarrow 0.5Ca^{2+} + PO_4^{3-} + 0.5OH^- \qquad (2)$$

This may be summarised by the general equation:

$$Ca_{10-y}Y_y(PO_4)_{6-x}(SiO_4)_x(OH)_{2-x+y}$$

(for this mechanism, y<x)

As for other ionic substitutions in the hydroxyapatite lattice, these substitutions have limits. When the levels of substitution pass these limits, the composition becomes thermally unstable during sintering, and phase decomposition of the hydroxyapatite occurs, leading to the formation of secondary phases. The co-substituted method according to the present invention may be used to increase the limit of silicate substitution into the hydroxyapatite lattice, without resulting in phase decomposition after sintering at typical temperatures (approximately 1200° C. or more), to a maximum of approximately 12 wt. % silicate ions (or 3.66 wt. % silicon). After this limit has been reached, secondary phases are produced. For certain applications, an essentially phase pure material is desired, and so the maximum of approximately 12 wt. % silicate ions will be adopted. For other applications, the presence of secondary phases may actually be desired (or may not present a problem), and the limit of approximately 12 wt. % silicate may then be exceeded.

The present invention will now be further described with reference to the following examples.

EXAMPLE 1

Synthesis of $Y^{3+}/SiO_4^{4-}$ Co-substituted Hydroxyapatite (x=y=1.0)

The following method describes the synthesis of approx. 10 g of a $Y^{3+}/SiO_4^{4-}$ co-substituted hydroxyapatite by an aqueous precipitation method with the following substitution mechanism:

$$Ca_{10-y}Y_y(PO_4)_{6-x}(SiO_4)_x(OH)_{2-x+y}$$

where x=y=1.0

CaCO₃ was first de-carbonated overnight (16 hours) in a furnace at 900° C. The resulting CaO was then removed from the furnace and placed in a dessicator to cool. 5.0782 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form Ca(OH)₂. Meanwhile, 3.8361 g Y(NO₃)₃.6H₂O(YNH) was added to a beaker containing approx. 100 ml deionised water and was mixed until the YNH had completely dissolved. The YNH solution was then slowly poured into the Ca(OH)₂ suspension and this suspension was left to stir for approx. 30 minutes.

Figure 1:
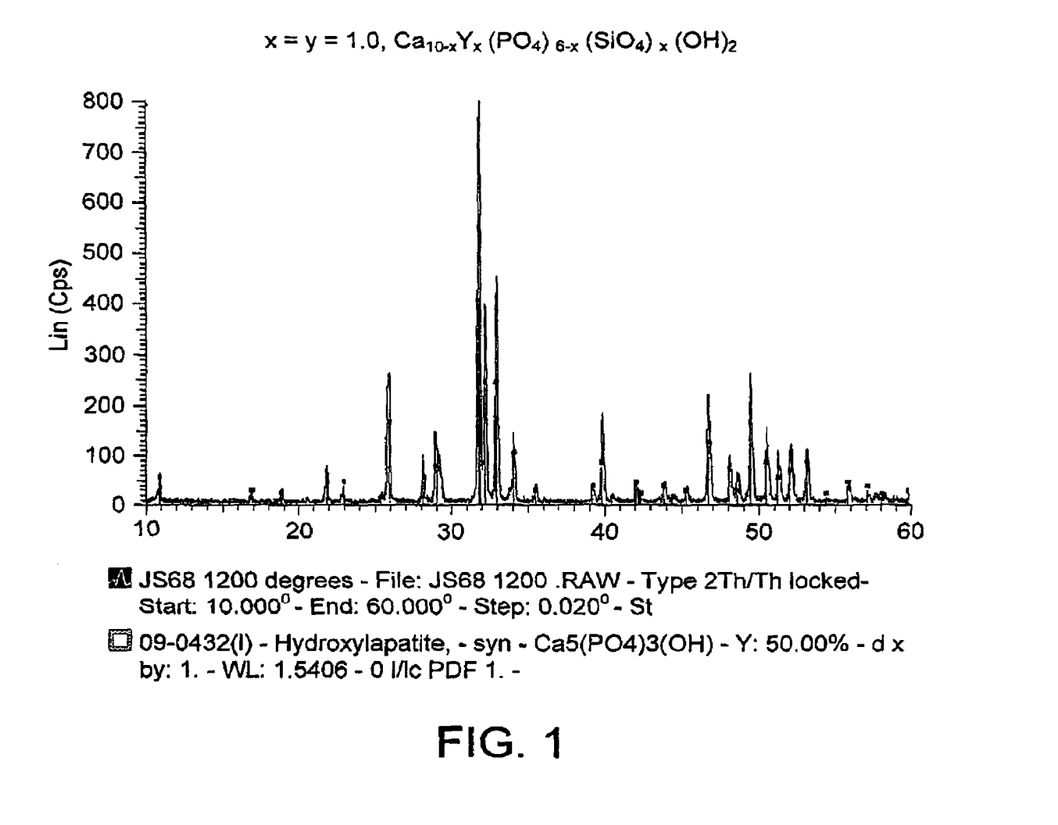
FIG. 1 is the X-ray diffraction of the sintered powder as described in Example 1.

5.7703 g H₃PO₄ (85% assay) was diluted with approx. 100 ml deionised water. This solution was poured into a dropping funnel and added drop-wise to the stirring Ca(OH)₂/YNH suspension over a period of approx. 30 minutes. After complete addition of the H₃PO₄ solution, 2.1278 g Si(OC₂H₅)₄ (TEOS) was diluted with approx. 100 ml deionised water and this solution was poured into a dropping funnel and added drop-wise to stirring Ca(OH)₂/YNH/H₃PO₄ mixture over a period of approx. 30 minutes. The pH of the stirring solution was monitored throughout the addition of the H₃PO₄ and TEOS solutions and was maintained at pH 12 by the addition of concentrated ammonia solution; in total, approx 37.5 ml was added. After complete addition of the TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively. The sintered powder was then analysed using X-ray diffraction to confirm the phase purity. A Bruker D8 diffractometer was used to collect data from 10 to 60° 2θ with a step size of 0.02° and a count time of 1.5 secs/step. The diffraction pattern obtained was compared with the ICDD (#09-0432) standard pattern for hydroxyapatite. All the diffraction peaks for the sintered $Y^{3+}/SiO_4^{4-}$ co-substituted hydroxyapatite matched the peaks of the ICDD standard, with no additional peaks observed, indicating that the composition produced by this method was a single-phase material with a hydroxyapatite-like structure (see FIG. 1).

EXAMPLE 2

Synthesis of $Y^{3+}/SiO_4^{4-}$ Co-substituted Hydroxyapatite (x=1.0, y=0.5)

The following method describes the synthesis of approx. 10 g of a $Y^{3+}/SiO_4^{4-}$ co-substituted hydroxyapatite by an aqueous precipitation method with the following substitution mechanism:

$$Ca_{10-y}Y_y(PO_4)_{6-x}(SiO_4)_x(OH)_{2-x+y}$$

where x=1.0, y=0.5

CaCO₃ was first de-carbonated overnight (16 hours) in a furnace at 900° C. The resulting CaO was then removed from the furnace and placed in a dessicator to cool. 5.3601 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form Ca(OH)₂. Meanwhile, 1.9162 g Y(NO₃)₃.6H₂O(YNH) was added to a beaker containing approx. 100 ml deionised water and was mixed until the YNH had completely dissolved. The YNH solution was then slowly poured into the Ca(OH)₂ suspension and this suspension was left to stir for approx. 30 minutes.

Figure 2:
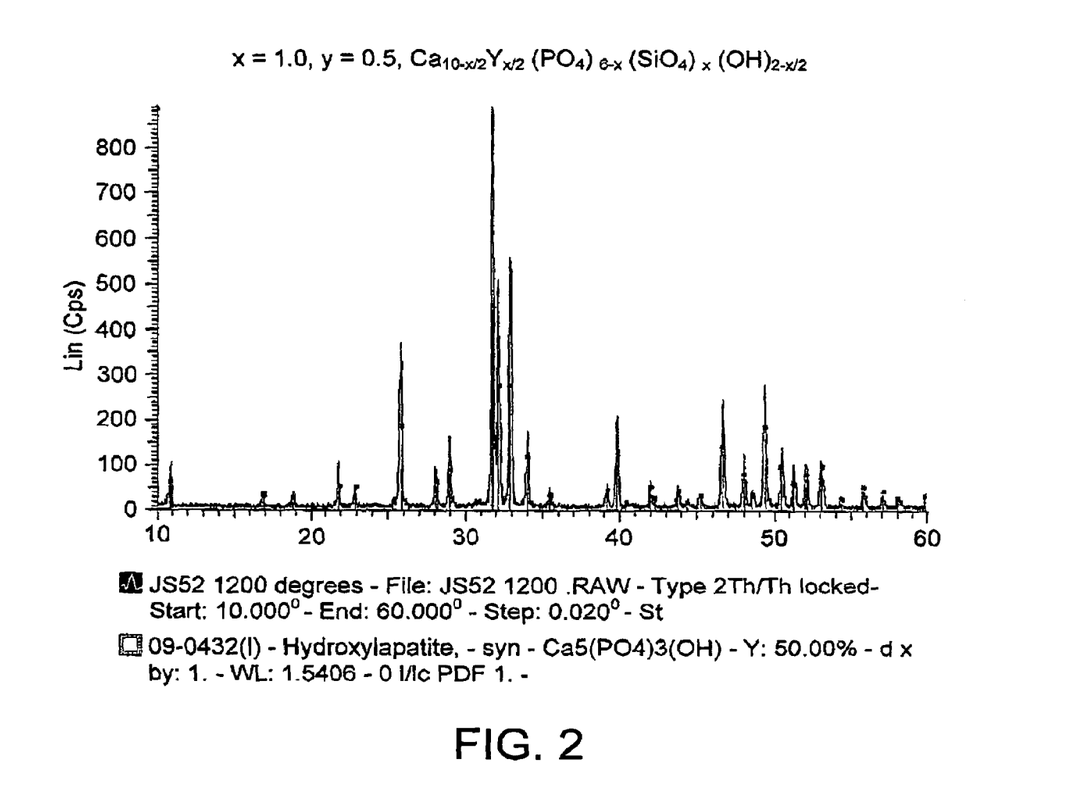
FIG. 2 is the X-ray diffraction of the sintered powder as described in Example 2.

5.7708 g $H_3PO_4$ (85% assay) was diluted with approx. 100 ml deionised water and this solution was poured into a dropping funnel. 2.1281 g $Si(OC_2H_5)_4$(TEOS) was diluted with approx. 100 ml deionised water and this solution was poured into the dropping funnel containing the $H_3PO_4$ solution, and this $H_3PO_4$/TEOS solution was added drop-wise to the stirring $Ca(OH)_2$/YNH suspension over a period of approx. 60 minutes. The pH of the stirring solution was monitored throughout the addition of the $H_3PO_4$/TEOS solution and was maintained at pH 12 by the addition of concentrated ammonia solution; in total, approx. 40 ml was added. After complete addition of the $H_3PO_4$/TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively. The sintered powder was then analysed using X-ray diffraction to confirm the phase purity. A Bruker D8 diffractometer was used to collect data from 10 to 60° 2θ with a step size of 0.02° and a count time of 1.5 secs/step. The diffraction pattern obtained was compared with the ICDD (#09-0432) standard pattern for hydroxyapatite. All the diffraction peaks for the sintered $Y^{3+}$/$SiO_4^{4-}$ co-substituted hydroxyapatite matched the peaks of the ICDD standard, with no additional peaks observed, indicating that the composition produced by this method was a single-phase material with a hydroxyapatite-like structure (see FIG. 2).

EXAMPLE 3

Synthesis of $Y^{3+}$/$SiO_4^{4-}$ Co-substituted Hydroxyapatite (x=y=1.0)

The synthesis in this example was exactly as for the synthesis method described in Example 1, except that the $H_3PO_4$ and TEOS solutions (approx. 100 ml each) were mixed together and added simultaneously in a drop-wise manner to the stirring $Ca(OH)_2$/YNH suspension over a period of approx. 60 minutes. Apart from this difference, the precipitation and subsequent processing steps were identical to those described in Example 1. The X-ray diffraction pattern of the sintered samples produced by this method were identical to that observed for Example 1.

EXAMPLE 4

Synthesis of $Y^{3+}$/$SiO_4^{4-}$ Co-substituted Hydroxyapatite/Tricalcium Phosphate Biphasic Mixture (x=0.6, y=0.6)

The following method describes the synthesis of approx. 10 g of a $Y^{3+}$/$SiO_4^{4-}$ co-substituted hydroxyapatite/tricalcium phosphate biphasic mixture by an aqueous precipitation method with the following substitution mechanism:

where x=y=0.6

To produce an yttria/silicate co-substituted biphasic composition, rather than a single phase yttria/silicate co-substituted hydroxyapatite composition (described in Example 1), the pH of the precipitation was lowered to 10, which promoted the precipitation of a yttria/silicate co-substituted cation-deficient apatite composition. This will form a biphasic yttria/silicate co-substituted composition on heating.

$CaCO_3$ was first de-carbonated overnight (16 hours) in a furnace at approx. 900° C. The resulting CaO was then removed from the furnace and placed in a dessicator to cool. 5.2735 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form $Ca(OH)_2$. Meanwhile, 2.2993 g $Y(NO_3)_3.6H_2O$ (YNH) was added to a beaker containing approx. 100 ml deionised water and was mixed until the YNH had completely dissolved. The YNH solution was then slowly poured into the $Ca(OH)_2$ suspension and this suspension was left to stir for approx. 30 minutes.

6.2286 g $H_3PO_4$ (85% assay) was diluted with approx. 100 ml deionised water and this solution was poured into a dropping funnel. 1.2764 g $Si(OC_2H_5)_4$(TEOS) was diluted with approx. 100 ml deionised water and this solution was poured into the dropping funnel containing the $H_3PO_4$ solution, and this $H_3PO_4$/TEOS solution was added drop-wise to the stirring $Ca(OH)_2$/YNH suspension over a period of approx. 60 minutes. The pH of the stirring solution was monitored throughout the addition of the $H_3PO_4$/TEOS solution and was maintained at pH 10 by the addition of concentrated ammonia solution; in total, approx. 10 ml was added. After complete addition of the $H_3PO_4$/TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively.

The sintered powder was then analysed using X-ray diffraction to confirm the phase purity. A Bruker D8 diffractometer was used to collect data from 10 to 60° 2θ with a step size of 0.02° and a count time of 1.5 secs/step.

Figure 3:
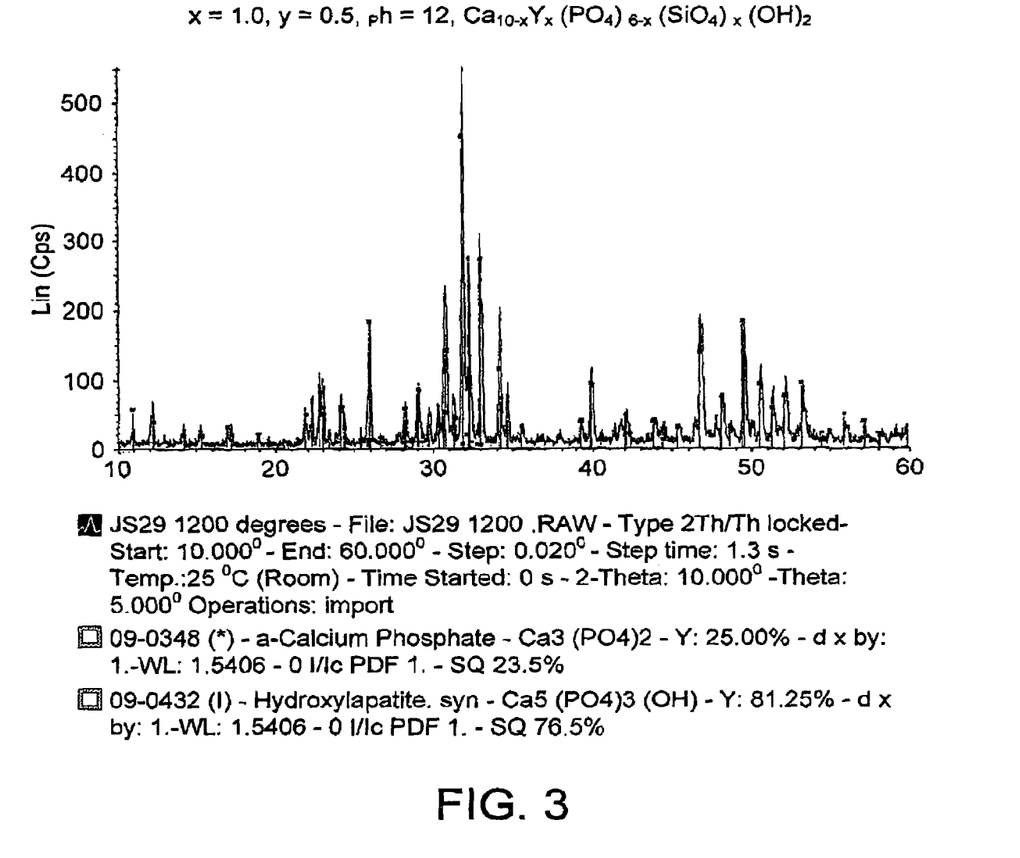
FIG. 3 is the X-ray diffraction of the sintered powder as described in Example 4.

The diffraction pattern obtained was compared with the ICDD (#09-0432) standard pattern for hydroxyapatite and (#09-0348) standard pattern for alpha-tricalcium phosphate. All the diffraction peaks for the sintered $Y^{3+}$/$SiO_4^{4-}$ co-substituted hydroxyapatite matched the peaks of the ICDD standard, matching both the hydroxyapatite phase and the alpha-tricalcium phosphate phase, indicating that the composition produced by this method was a biphasic material (see FIG. 3). Comparing the intensities of the most intense peaks of the hydroxyapatite and the alpha-tricalcium phosphate phases, the amount of hydroxyapatite is approximated at 70%, and the amount of tricalcium phosphate as 30%.

EXAMPLE 5

Synthesis of $Y^{3+}$/$SiO_4^{4-}$ Co-substituted Hydroxyapatite/Tricalcium Phosphate Biphasic Mixture (x=0.6, y=0.3)

The following method describes the synthesis of approx. 10 g of a $Y^{3+}$/$SiO_4^{4-}$ co-substituted hydroxyapatite/tricalcium phosphate biphasic mixture by an aqueous precipitation method with the following substitution mechanism:

where x=0.6, y=0.3

To produce an yttria/silicate co-substituted biphasic composition with y<x, rather than a single phase yttria/silicate co-substituted hydroxyapatite composition (described in Example 2) the pH of the precipitation was lowered to 10, which promoted the precipitation of a yttria/silicate co-substituted cation-deficient apatite composition. This will form a biphasic yttria/silicate co-substituted composition on heating.

$CaCO_3$ was first de-carbonated overnight (16 hours) in a furnace at 900° C. The resulting CaO was then removed from the furnace and placed in a dessicator to cool. 5.4461 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form $Ca(OH)_2$. Meanwhile, 1.1508 g $Y(NO_3)_3.6H_2O$(YNH) was added to a beaker containing approx. 100 ml deionised water and was mixed until the YNH had completely dissolved. The YNH solution was then slowly poured into the $Ca(OH)_2$ suspension and this suspension was left to stir for approx. 30 minutes.

6.2264 g $H_3PO_4$ (85% assay) was diluted with approx. 100 ml deionised water and this solution was poured into a dropping funnel. 1.2817 g $Si(OC_2H_5)_4$(TEOS) was diluted with approx. 100 ml deionised water and this solution was poured into the dropping funnel containing the $H_3PO_4$ solution, and this $H_3PO_4$/TEOS solution was added drop-wise to the stirring $Ca(OH)_2$/YNH suspension over a period of approx. 60 minutes. The pH of the stirring solution was monitored throughout the addition of the $H_3PO_4$/TEOS solution and was maintained at pH 10 by the addition of concentrated ammonia solution; in total, approx. 10 ml was added. After complete addition of the $H_3PO_4$/TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively.

Figure 4:
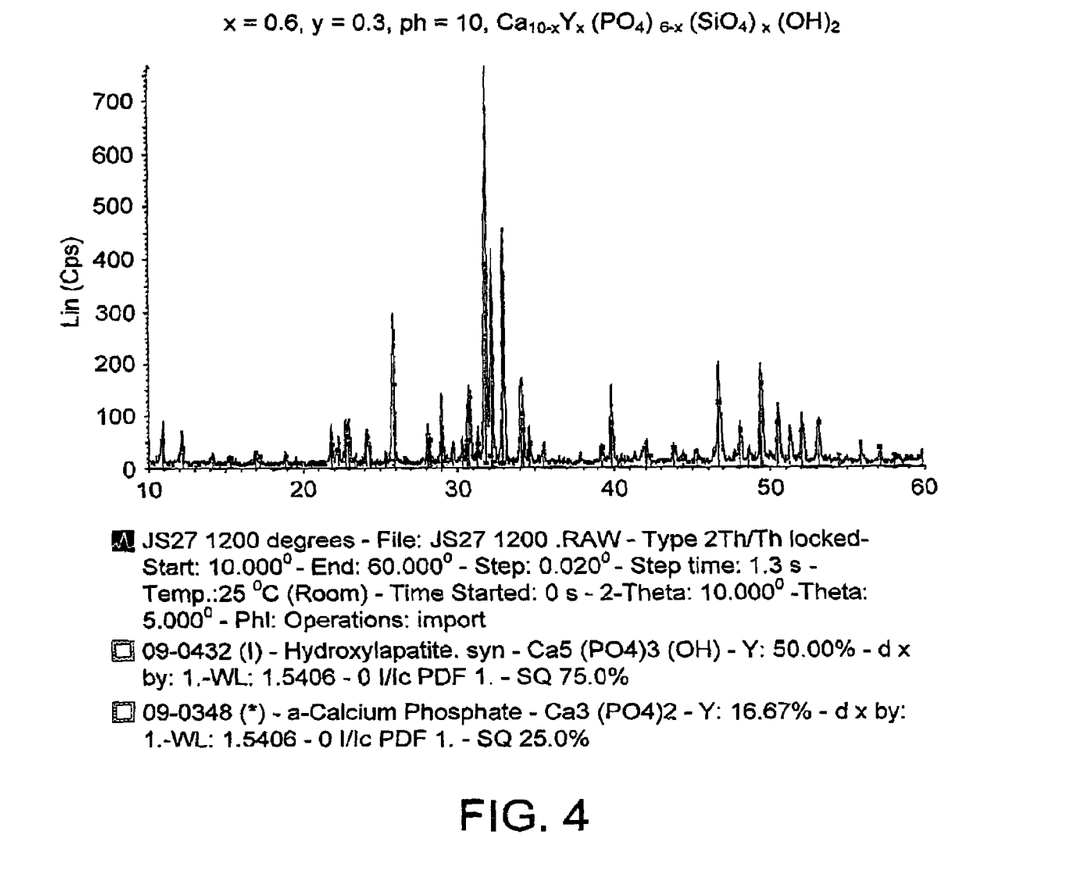
FIG. 4 is the X-ray diffraction of the sintered powder as described in Example 5.

The sintered powder was then analysed using X-ray diffraction to confirm the phase purity. A Bruker D8 diffractometer was used to collect data from 10 to 60° 2θ with a step size of 0.02° and a count time of 1.5 secs/step. The diffraction pattern obtained was compared with the ICDD (#09-0432) standard pattern for hydroxyapatite and (#09-0348) standard pattern for alpha-tricalcium phosphate. All the diffraction peaks for the sintered $Y^{3+}/SiO_4^{4-}$ co-substituted hydroxyapatite matched the peaks of the ICDD standard, matching both the hydroxyapatite phase and the alpha-tricalcium phosphate phase, indicating that the composition produced by this method was a biphasic material (see FIG. 4). Comparing the intensities of the most intense peaks of the hydroxyapatite and the alpha-tricalcium phosphate phases, the amount of hydroxyapatite is approximated at 85%, and the amount of tricalcium phosphate as 15%.

EXAMPLE 6

Synthesis of $Y^{3+}/SiO_4^{4-}$ Co-substituted Hydroxyapatite/Tricalcium Phosphate Biphasic Mixture (x=y=1.3)

The following method describes the synthesis of approx. 10 g of a $Y^{3+}/SiO_4^{4-}$ co-substituted hydroxyapatite/tricalcium phosphate biphasic mixture by an aqueous precipitation method with the following substitution mechanism:

$Ca_{10-y}Y_y(PO_4)_{6-x}(SiO_4)_x(OH)_{2-x+y}$ where x=y=1.3

To produce an yttria/silicate co-substituted biphasic composition, rather than a single phase yttria/silicate co-substituted hydroxyapatite composition (described in Example 1), but at pH 12, a deficient amount of $Ca(OH)_2$ and YNH was added, which promoted the precipitation of a yttria/silicate co-substituted cation-deficient apatite composition. This will form a biphasic yttria/silicate co-substituted composition on heating.

$CaCO_3$ was first de-carbonated overnight (16 hours) in a furnace at 900° C. The resulting CaO was then removed from the furnace and placed in a dessicator to cool. 4.9054 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form $Ca(OH)_2$. Meanwhile, 4.9807 g $Y(NO_3)_3.6H_2O$(YNH) was added to a beaker containing approx. 100 ml deionised water and was mixed until the YNH had completely dissolved. The YNH solution was then slowly poured into the $Ca(OH)_2$ suspension and this suspension was left to stir for approx. 30 minutes.

5.4277 g $H_3PO_4$ (85% assay) was diluted with approx. 100 ml deionised water and this solution was poured into a dropping funnel. 2.7679 g $Si(OC_2H_5)_4$(TEOS) was diluted with approx. 100 ml deionised water and this solution was poured into the dropping funnel containing the $H_3PO_4$ solution, and this $H_3PO_4$/TEOS solution was added drop-wise to the stirring $Ca(OH)_2$/YNH suspension over a period of approx. 60 minutes. The pH of the stirring solution was monitored throughout the addition of the $H_3PO_4$/TEOS solution and was maintained at pH 12 by the addition of concentrated ammonia solution; in total, approx. 40 ml was added. After complete addition of the $H_3PO_4$/TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively.

Figure 5:
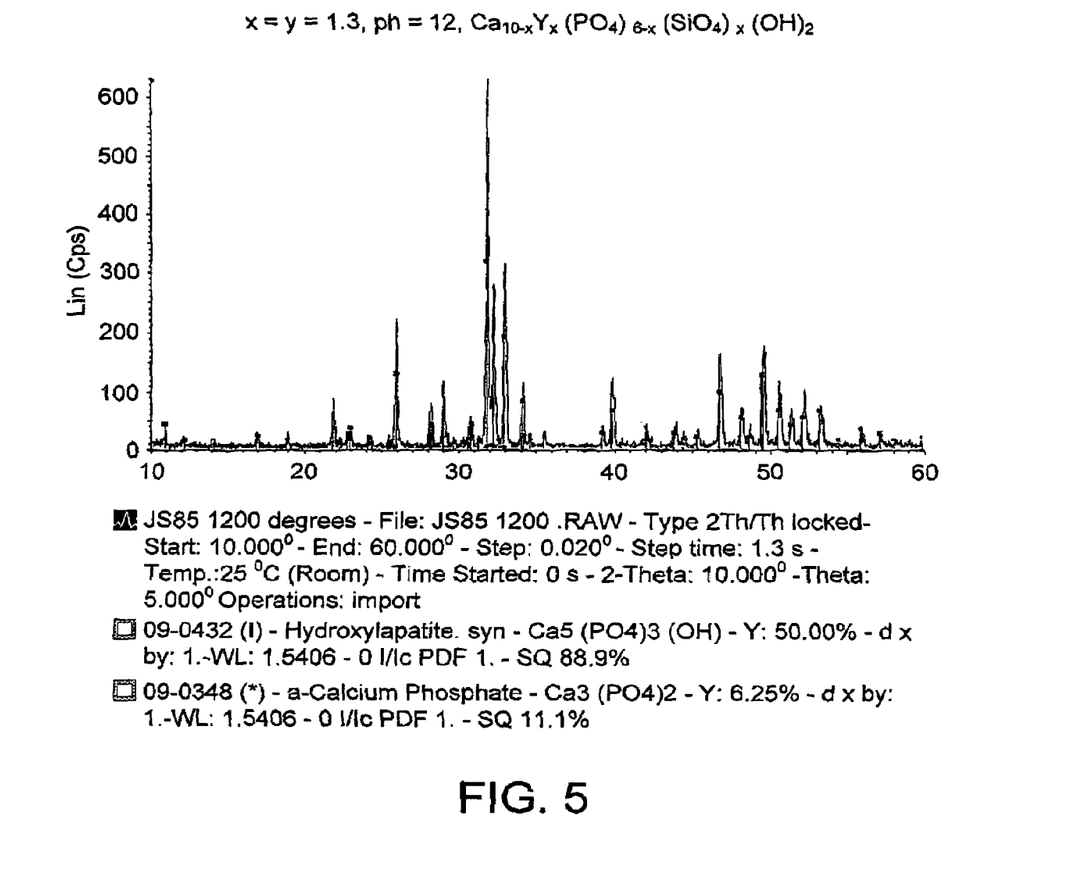
FIG. 5 is the X-ray diffraction of the sintered powder as described in Example 6.

The sintered powder was then analysed using X-ray diffraction to confirm the phase purity. A Bruker D8 diffractometer was used to collect data from 10 to 60° 2θ with a step size of 0.02° and a count time of 1.5 secs/step. The diffraction pattern obtained was compared with the ICDD (#09-0432) standard pattern for hydroxyapatite and (#09-0348) standard pattern for alpha-tricalcium phosphate. All the diffraction peaks for the sintered $Y^{3+}/SiO_4^{4-}$ co-substituted hydroxyapatite matched the peaks of the ICDD standard, matching both the hydroxyapatite phase and the alpha-tricalcium phosphate phase, indicating that the composition produced by this method was a biphasic material (see FIG. 5). Comparing the intensities of the most intense peaks of the hydroxyapatite and the alpha-tricalcium phosphate phases, the amount of hydroxyapatite is approximated at 90%, and the amount of tricalcium phosphate as 10%.

EXAMPLE 7

Synthesis of $Y^{3+}/SiO_4^{4-}$ Co-substituted Hydroxyapatite/Tricalcium Phosphate Biphasic Mixture (x=1.0, y=0.5)

The following method describes the synthesis of approx. 10 g of a $Y^{3+}/SiO_4^{4-}$ co-substituted hydroxyapatite/trical cium phosphate biphasic mixture by an aqueous precipitation method with the following substitution mechanism:

$$Ca_{10-y}Y_y(PO_4)_{6-x}(SiO_4)_x(OH)_{2-x+y}$$

where x=1.0, y=0.5

To produce an yttria/silicate co-substituted biphasic composition with y<x, rather than a single phase yttria/silicate co-substituted hydroxyapatite composition (described in Example 2), but at pH 12, a deficient amount of Ca(OH)$_2$ and YNH was added, which promoted the precipitation of a yttria/silicate co-substituted cation-deficient apatite composition. This will form a biphasic yttria/silicate co-substituted composition on heating.

CaCO$_3$ was first de-carbonated overnight (16 hours) in a furnace at 900° C. The resulting CaO was then removed from the furnace and placed in a dessicator to cool. 5.3299 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form Ca(OH)$_2$. Meanwhile, 1.9170 g Y(NO$_3$)$_3$.6H$_2$O(YNH) was added to a beaker containing approx. 100 ml deionised water and was mixed until the YNH had completely dissolved. The YNH solution was then slowly poured into the Ca(OH)$_2$ suspension and this suspension was left to stir for approx. 30 minutes.

5.7719 g H$_3$PO$_4$ (85% assay) was diluted with approx. 100 ml deionised water and this solution was poured into a dropping funnel. 2.1259 g Si(OC$_2$H$_5$)$_4$(TEOS) was diluted with approx. 100 ml deionised water and this solution was poured into the dropping funnel containing the H$_3$PO$_4$ solution, and this H$_3$PO$_4$/TEOS solution was added drop-wise to the stirring Ca(OH)$_2$/YNH suspension over a period of approx. 60 minutes. The pH of the stirring solution was monitored throughout the addition of the H$_3$PO$_4$/TEOS solution and was maintained at pH 12 by the addition of concentrated ammonia solution; in total, approx. 40 ml was added. After complete addition of the H$_3$PO$_4$/TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 2.5 and 10°/min, respectively.

Figure 6:
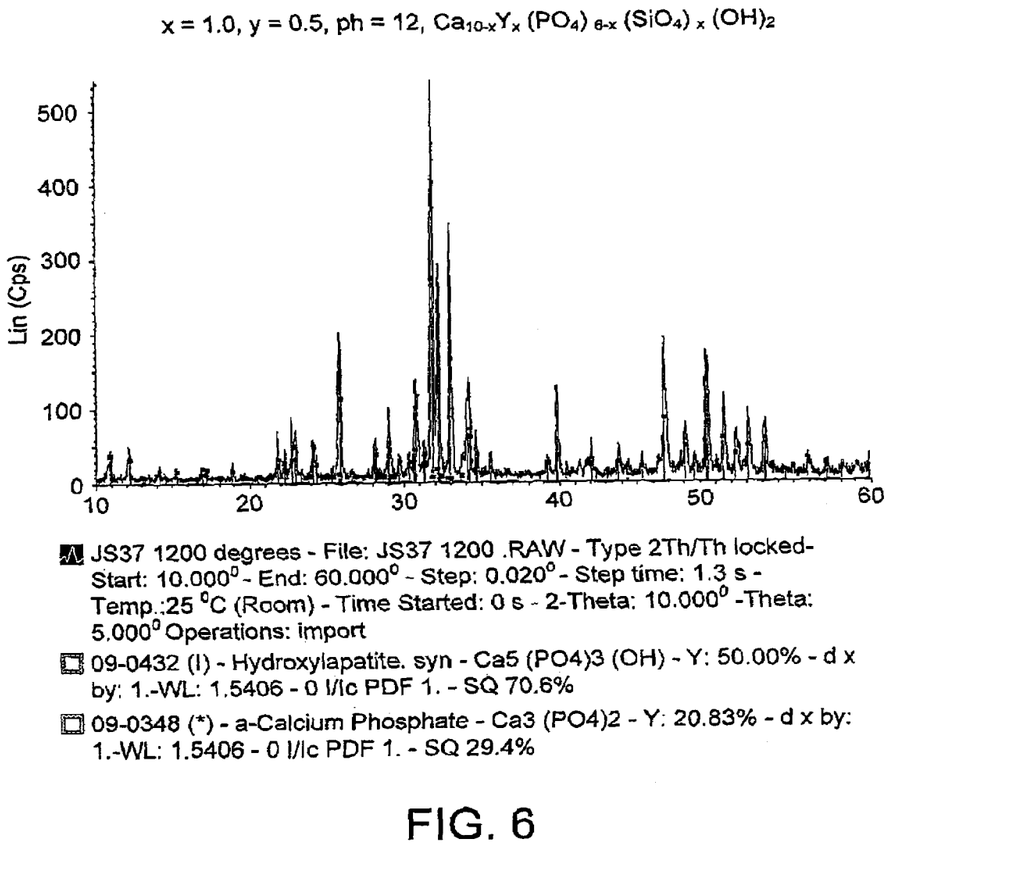
FIG. 6 is the X-ray diffraction of the sintered powder as described in Example 7.

The sintered powder was then analysed using X-ray diffraction to confirm the phase purity. A Bruker D8 diffractometer was used to collect data from 10 to 60° 2θ with a step size of 0.02° and a count time of 1.5 secs/step. The diffraction pattern obtained was compared with the ICDD (#09-0432) standard pattern for hydroxyapatite and (#09-0348) standard pattern for alpha-tricalcium phosphate. All the diffraction peaks for the sintered Y$^{3+}$/SiO$_4^{4-}$ co-substituted hydroxyapatite matched the peaks of the ICDD standard, matching both the hydroxyapatite phase and the alpha-tricalcium phosphate phase, indicating that the composition produced by this method was a biphasic material (see FIG. 6). Comparing the intensities of the most intense peaks of the hydroxyapatite and the alpha-tricalcium phosphate phases, the amount of hydroxyapatite is approximated at 80%, and the amount of tricalcium phosphate as 20%.

The present invention enables greater levels of silicate ions (or silicon) to be substituted into the calcium phosphate (eg hydroxyapatite or apatite) lattice without any significant phase decomposition at typical sintering temperatures, for example ≧1200° C. As a consequence, the current substitution limit of 5.3 wt % silicate (or 1.6 wt % silicon) may be increased, which results in a synthetic biomedical material that more closely matches the chemical composition of bone mineral. The present invention also enable the production of biphasic and multiphase materials with even higher silicon contents.

The invention claimed is:

1. A synthetic calcium phosphate-based biomedical material comprising silicon and a trivalent cation wherein the material comprises a compound having the chemical formula:

$$Ca_{10-y}M_y(PO_4)_{6-x}(SiO_4)_x(OH)_{2-x+y}$$

where M is a trivalent cation, 0<x<1.3 and 0<y<1.3 and wherein the trivalent cation is selected from one or more of yttrium, scandium, aluminum and the Lanthanide elements.

2. The biomedical material according to claim 1, wherein the calcium phosphate-based biomedical material comprises hydroxyapatite or apatite.

3. The biomedical material according to claim 1, wherein 0<x<1.1.

4. The biomedical material according to claim 3, wherein 0.5<x<1.1.

5. The biomedical material according to claim 1, wherein 0<y<1.1.

6. The biomedical material according to claim 5, wherein 0.5<y<1.1.

7. The biomedical material according to claim 1, wherein x≧y.

8. The biomedical material according to claim 1, wherein y≧x.

9. The biomedical material according to claim 1, wherein the phase purity of the biomedical material, as measured by X-ray diffraction, is at least 95%.

10. The biomedical material according to claim 1, wherein the biomedical material comprises one or more secondary phases.

11. The biomedical material according to claim 10, wherein the secondary phases comprise one or more of tri-calcium phosphate, alpha or beta polymorphs thereof, calcium silicate, tetracalcium phosphate, calcium carbonate, calcium oxide, monetite, brushite, calcium pyrophosphate and octacalcium phosphate.

12. The biomedical material according to claim 1, wherein the trivalent cation is yttrium.

13. A synthetic bone material, bone implant, bone graft, bone substitute, bone scaffold, filler, coating or cement comprising a biomedical material as defined in claim 1.

14. A process for the synthesis of a calcium phosphate-based material of claim 1 comprising silicon and a trivalent cation, the process comprising:
   providing calcium or a calcium-containing compound, a trivalent cation-containing compound, a phosphorus-containing compound and a silicon-containing compound; and
   forming a precipitate by reacting the compounds in an aqueous phase at an alkali pH.

15. The process according to claim 14, wherein the calcium phosphate-based material comprises hydroxyapatite or apatite.

16. The process according to claim 14, wherein the calcium-containing compound comprises a calcium salt.

17. The process according to claim 16, wherein the calcium salt is selected from one or more of calcium hydroxide, calcium chloride, calcium nitrate and/or calcium nitrate hydrate.

18. The process according to claim 14, wherein the trivalent cation-containing compound comprises a compound of yttrium.

19. The process according to claim 18, wherein the yttrium compound is selected from one or both of yttrium chloride and/or yttrium nitrate.

20. The process according to claim 18, wherein yttrium is present in the material in an amount of up to 13 weight percent.

21. The process according to claim 18, wherein yttrium is present in the material in an amount of up to 20 weight percent.

22. The process according to claim 14, wherein the phosphorus-containing compound is selected from one or both of a phosphate salt and/or a phosphoric acid.

23. The process according to claim 22, wherein the phosphorus-containing compound is selected from one or both of ammonium phosphate and/or phosphoric acid.

24. The process according to claim 14, wherein the silicon-containing compound comprises a silicate.

25. The process according to claim 24, wherein the silicate is selected from one or both of tetraethyl orthosilicate (TEOS) and/or silicon acetate.

26. The process according to claim 24, wherein the silicate is present in the material in an amount of up to 13 weight percent.

27. The process according to claim 24, wherein the silicate is present in the material in an amount of up to 20 weight percent.

28. The process according to claim 14, wherein the pH is from 8 to 13.

29. The process according to claim 28, wherein the pH is from 10 to 12.

30. The process according to claim 14, wherein an alkali is added to adjust the pH of the solution to the desired pH.

31. The process according to claim 30, wherein the alkali is ammonium hydroxide or concentrated ammonia.

32. The process according to claim 14, wherein after the precipitate has been formed it is dried, heated and/or sintered.

33. The process according to claim 32, wherein the precipitate is heated and/or sintered to a temperature in the range of from 800° C. to 1500° C.

34. The process according to claim 33, wherein the precipitate is heated and/or sintered to a temperature in the range of from 1000° C. to 1350° C., preferably from 1200° C. to 1300° C.

35. The process according to claim 14, wherein the silicon-containing and the trivalent cation-containing compounds are supplied in equimolar quantities with respect to the amount of silicon and the quantity of the trivalent cation.

36. The process according to claim 14, wherein the silicon-containing compound is supplied in a greater quantity than the trivalent cation compound with respect to the quantity of silicon and the quantity of the trivalent cation.

37. The process according to claim 14, wherein the silicon-containing compound is supplied in a lesser quantity than the trivalent cation compound with respect to the quantity of silicon and the quantity of the trivalent cation.

38. A method of stabilizing a silicon-substituted calcium phosphate material of claim 1, characterized by substituting a trivalent cation into the lattice.

39. The method according to claim 38, wherein the calcium phosphate material comprises hydroxyapatite or apatite.

40. The method according to claim 38, wherein the trivalent cation is yttrium.

41. The biomedical material according to claim 1, wherein the phase purity of the biomedical material, as measured by X-ray diffraction, is at least 97%.

42. The biomedical material according to claim 1, wherein the phase purity of the biomedical material, as measured by X-ray diffraction, is at least 99%.

43. The process according to claim 18, wherein yttrium is present in the material in an amount of up to 12 weight percent.

44. The process according to claim 24, wherein the silicate is present in the material in an amount of up to 12 weight percent.

45. The biomedical material of claim 1, wherein the silicate is present in the material in an amount of up to 12 weight percent.

46. The biomedical material according to claim 1, wherein the trivalent cation is yttrium.

47. The process of claim 24, wherein the silicate is present in the material in an amount of greater than 5.3 weight percent and up to 13 weight percent.

48. The process of claim 24, wherein the silicate is present in the material in an amount of greater than 5.3 weight percent and up to 12 weight percent.

49. The process of claim 24, wherein the silicate is present in the material in an amount of greater than 13 weight percent and up to 20 weight percent.

50. The biomedical material of claim 1, wherein the silicate is present in the material in an amount of greater than 5.3 weight percent and up to 13 weight percent.

51. The biomedical material of claim 1, wherein the silicate is present in the material in an amount of greater than 5.3 weight percent and up to 12 weight percent.

52. The biomedical material of claim 1, wherein the silicate is present in the material in an amount of greater than 13 weight percent and up to 20 weight percent.

* * * * *